US00PP11849P2

(12) United States Plant Patent
Zary

(10) Patent No.: US PP11,849 P2
(45) Date of Patent: Apr. 24, 2001

(54) SHRUB ROSE PLANT NAMED 'JACSUYEL'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/266,992

(22) Filed: Mar. 12, 1999

(51) Int. Cl.[7] ..... A01H 5/00

(52) U.S. Cl. ..... Plt./105

(58) Field of Search ..... Plt./102, 105, 112, Plt./135, 146

*Primary Examiner*—Howard J. Locker
(74) *Attorney, Agent, or Firm*—Klarquist Sparkman Campbell Leigh & Whinston, LLP

(57) ABSTRACT

A shrub rose plant characterized by its vigorous, upright growth with fairly small, healthy, dark green foliage; its large clusters of bright copper yellow flowers and ability to root from softwood and hardwood cuttings.

1 Drawing Sheet

The present invention relates to a new and distinct variety of rose plant of the shrub class which was originated by me by crossing the variety 'JACjem', U.S. Plant Pat. No. 5,001, with an unnamed seeding (unnamed seedling×Golden Showers, U.S. Plant Pat. No. 1,557).

The primary objective of this breeding was to produce a new rose variety having the large flower size and multiple petalled characteristic of the female parent as well as its clustering ability and healthy foliage with the vigorous, tall growth, large clusters of dark gold yellow color flowers and healthy, glossy foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Fairly small, healthy, dark green foliage;
2. Bright copper yellow flower color;
3. Vigorous, upright growth;
4. Ability to root from softwood and hardwood cuttings; and
5. Flowers with 20 to 25 petals.

'JACsuyel' is a tall growing shrub garden rose. It flowers in large clusters and breaks freely below the flowering cluster with new flowering shoots. This insures it is in constant flower during the growing season.

Asexual reproduction of this new variety by cuttings (both softwood and hardwood) and by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACjem', U.S. Plant Pat. No. 5,001.

*Pollen parent.*—Unnamed seedling (Unnamed seedling×Golden Showers, U.S. Plant Pat. No. 1,557).

Classification:

*Botanical.*—*Rosa hybrida.*

*Commercial.*—Shrub.

FLOWER

Observations made from specimens grown in a garden environment at Somis, Calif. in March 1997 to November 1998.

Blooming habit: Continuous.

Bud:

*Size.*—One inch long when the petals start to unfurl.

*Form.*—The bud form is long, pointed ovoid.

*Color.*—When sepals first divide, bud color is Yellow-Orange Group 22C with the tip of the bud Orange Group 29C. When half blown, the upper sides of the petals are Yellow-Orange Group 22C with a blush of Orange Group 29D over the outer three-fourths of the petal; and the lower sides of the petals are Yellow-Orange Group 22C with Orange Group 29D on the edge of the petal.

*Sepals.*—Color: Green Group 138B. Surface texture: Covered in fine hairs. There are three lightly to normally appendaged sepals. There are two unappendaged sepals with hairy edges.

*Receptacle.*—Color: Green Group 137C. Shape: Funnel. Size: Small (5/16"×1/4"). Surface: Smooth.

*Peduncle.*—Length: Short, averaging about 1 to 1½ inches. Surface: Glandular. Color: Yellow-Green Group 146B with some Greyed-Purple Group 183C. Strength: Stiff, erect.

Bloom:

*Size.*—Small. Average open size is three inches.

*Borne.*—Several together in clusters of five to nine blooms having pyramidal shape.

*Stems.*—Strength: Strong. Average length is about 18 to 24 inches.

*Form.*—When first open: High centered. Permanence: Flattens, all petals curl.

*Petalage.*—Number of petals under normal conditions: 20 to 25.

*Color.*—The upper sides of the petals are Yellow-Orange Group 22C with a blush of Orange Group 29D over the outer three-fourths of the petal. The reverse sides of the petals are Yellow-Orange Group 22C with Orange Group 29D on the edge of the petal. The base of each petal has on the upper and lower surfaces a small (1/16"×1/16") Yellow-Orange Group 17C color spot. The major color on the upper side is Yellow-Orange Group 22C.

*Variegations.*—None.

*Discoloration.*—The general tonality at the end of the first day: No change. At the end of the third day: No change.

*Fragrance.*—Slight.

Petals:

*Texture.*—Thick.

*Shape.*—Oval to deltoid.

*Form.*—Tips slightly recurved.

*Arrangement.*—Imbricated. Petaloids in the center are few, range from one to five. Color: Yellow-Orange Group 22C. Size: 1/4 inch to 1/2 inch long and 1/8 to 1/4 inch wide.

*Persistence.*—Petals drop off cleanly before drying.

*Lastingness.*—On the plant: Short (about four to five days). As a cut flower: Not tested.

Reproductive parts:

*Anthers.*—Size: Medium. Quantity: Many. Color: Orange-Yellow Group 23C. Arrangement: Regular around styles.

*Filaments.*—Color: Yellow-Orange Group 23A.

*Pollen.*—Present.

*Styles.*—Color: Red Group 53B.

*Stigmas.*—Color: Orange-White Group 159A.

Plant:

*Form.*—Shrub.

*Growth.*—Very vigorous, upright, branching. At maturity, height is 5½ to 6 feet, width is 3½ to 4 feet.

Foliage: Number of leaflets on normal mid-stem leaves: Five.

*Size.*—Medium (5 inches long×4 inches wide).

*Quantity.*—Abundant.

*Color.*—New foliage: Upper and lower surfaces: Greyed-Red Group 178C, very rapidly turns green. Old foliage: Upper surface: Green Group 136A. Lower surface: Green Group 137A.

Leaflets:

*Shape.*—Pointed oval.

*Texture.*—Leathery, glossy.

*Edge.*—Serrated.

*Serration.*—Single, small.

*Petiole rachis.*—Color: Upper — Greyed-Purple Group 183A. Lower — Yellow-Green Group 146B with a blush of Greyed-Purple Group 183D.

*Petiole underside.*—Rough with prickles.

*Stipules.*—Long, serrated (about 7/8 inch), bearded.

*Disease resistance.*—Mildew and rust resistant but susceptible to blackspot under normal growing conditions.

Wood:

*New wood.*—Color: Yellow-Green Group 146C. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium, hooked downward.

*Color when young.*—Greyed-Red Group 178A.

*Color when mature.*—Greyed-Orange Group 173C.

Small prickles:

*Quantity.*—On main stalks: None. On laterals: None.

I claim:

1. A new and distinct variety of rose plant of the shrub class, substantially as herein shown and described, characterized particularly by its vigorous, upright growth with fairly small, healthy, dark green foliage; its large clusters of bright copper yellow flowers and ability to root from softwood and hardwood cuttings.

* * * * *

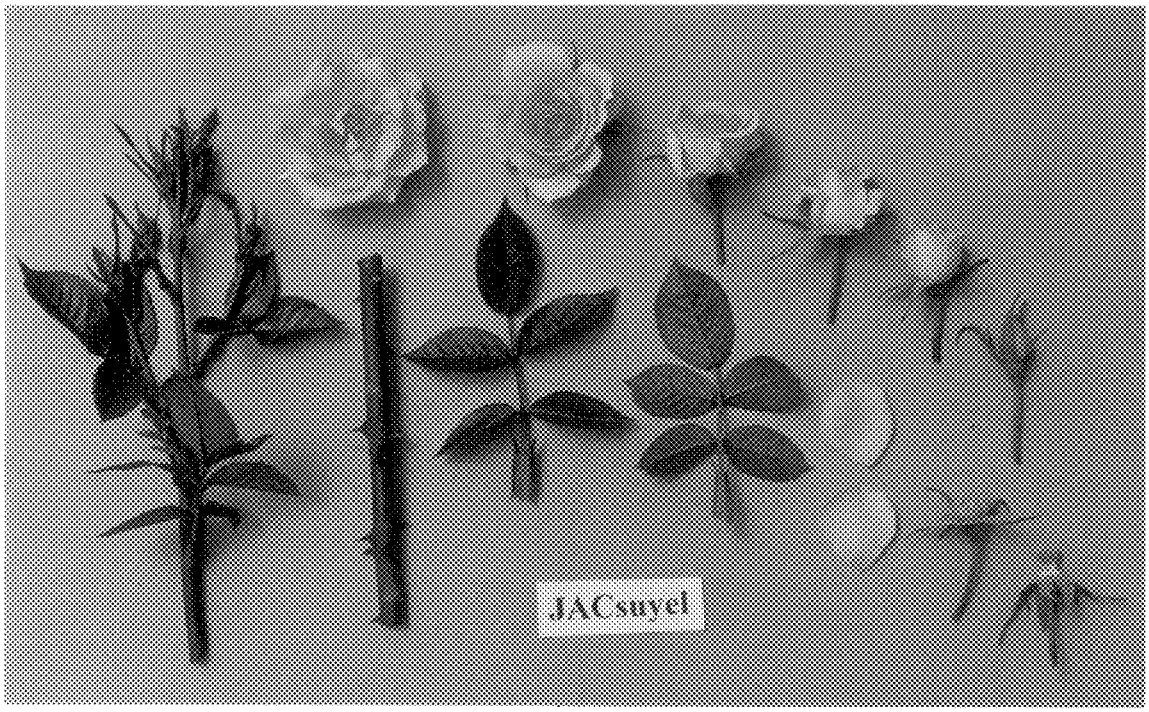
JACsuyel